US010857301B2

(12) United States Patent
Loonan

(10) Patent No.: US 10,857,301 B2
(45) Date of Patent: Dec. 8, 2020

(54) SYRINGE WITH POSITION LOCKING PLUNGER

(71) Applicant: Howard Loonan, Hillsborough, NJ (US)

(72) Inventor: Howard Loonan, Hillsborough, NJ (US)

(73) Assignee: Endospace Corporation, Newport, DE (US)

( * ) Notice: Subject to any disclaimer, the term of this patent is extended or adjusted under 35 U.S.C. 154(b) by 121 days.

(21) Appl. No.: 15/710,372

(22) Filed: Sep. 20, 2017

(65) Prior Publication Data
US 2018/0078707 A1 Mar. 22, 2018

Related U.S. Application Data

(60) Provisional application No. 62/396,876, filed on Sep. 20, 2016.

(51) Int. Cl.
*A61M 5/315* (2006.01)

(52) U.S. Cl.
CPC ...... *A61M 5/31501* (2013.01); *A61M 5/3158* (2013.01); *A61M 5/31571* (2013.01); *A61M 2005/31508* (2013.01)

(58) Field of Classification Search
CPC .. A61M 5/31501; A61M 5/3205; A61M 5/50; A61M 5/3129; A61M 5/31511; A61M 5/31505; A61M 5/3151; A61M 5/46; A61M 5/281; A61M 5/31568; A61M 5/3157; A61M 5/31571; A61M 5/31573; A61M 5/3153; A61M 5/31536; A61M 2005/3142
See application file for complete search history.

(56) References Cited

U.S. PATENT DOCUMENTS

| 2,895,773 A * | 7/1959 | McConnaughey ......................... A61M 5/31515 92/245 |
| 4,333,458 A | 6/1982 | Margulies et al. |
| 4,386,606 A | 6/1983 | Tretinyak et al. |
| 4,610,672 A | 9/1986 | Ewalt et al. |
| 4,711,637 A | 12/1987 | Leigh et al. |
| 4,766,906 A | 8/1988 | Wang |
| 5,215,536 A * | 6/1993 | Lampropoulos ...... A61M 5/315 604/187 |

(Continued)

FOREIGN PATENT DOCUMENTS

| CN | 1217942 | 6/1999 |
| CN | 2325032 | 6/1999 |

(Continued)

*Primary Examiner* — Brandy S Lee
*Assistant Examiner* — Nidah M Hussain
(74) *Attorney, Agent, or Firm* — Gearhart Law LLC

(57) ABSTRACT

The present disclosure provides for a syringe that is designed to enable a plunger to be locked or secured in position thereby freeing a user's hand from the plunger for other tasks. The syringe may be coupled to a needle or hypodermic needle or other apparatus such as an intravenous line/port or catheter. The syringe takes advantage of a tapered barrel and a positive stop to prevent movement of the piston along the inner surface of the barrel when no force is being actively applied to the plunger. This prevents unwanted suction or spillage of the contents contained therein.

17 Claims, 2 Drawing Sheets

(56) References Cited

U.S. PATENT DOCUMENTS

| | | | |
|---|---|---|---|
| 5,685,864 A * | 11/1997 | Shanley | A61M 5/31586 604/187 |
| 5,709,253 A | 1/1998 | Maerzke | |
| 5,735,825 A | 4/1998 | Stevens et al. | |
| 6,991,618 B2 | 1/2006 | Lau et al. | |
| 7,470,259 B2 | 12/2008 | Hoyle, Jr. | |
| 7,740,610 B2 | 6/2010 | Moh et al. | |
| 8,353,878 B2 | 1/2013 | Moller et al. | |
| 8,469,233 B2 | 6/2013 | Lutz et al. | |
| 9,186,463 B2 | 11/2015 | Hoyle, Jr. | |
| 9,192,727 B2 | 11/2015 | Meller et al. | |
| 9,205,205 B2 | 12/2015 | Burns et al. | |
| 9,265,880 B1 | 2/2016 | Wong et al. | |
| 9,333,301 B2 | 5/2016 | Alheidt et al. | |
| 9,352,093 B2 | 5/2016 | Crapser | |
| 2003/0105433 A1 | 6/2003 | Ruben | |
| 2003/0195477 A1 | 10/2003 | Ruben | |
| 2011/0087173 A1 | 4/2011 | Sibbitt, Jr. et al. | |
| 2012/0316509 A1 | 12/2012 | Kayser et al. | |
| 2013/0197449 A1 * | 8/2013 | Franklin | A61M 5/31595 604/209 |
| 2015/0105754 A1 | 4/2015 | Roche et al. | |
| 2018/0015227 A1 * | 1/2018 | Al-Omar | A61M 5/31595 |

FOREIGN PATENT DOCUMENTS

| | | |
|---|---|---|
| CN | 201290922 | 8/2009 |
| CN | 201505349 | 6/2010 |
| CN | 201840707 | 5/2011 |
| CN | 202961309 | 6/2013 |
| CN | 203196037 | 9/2013 |
| CN | 204910250 | 12/2015 |
| CN | 105662485 | 6/2016 |
| DE | 19710756 | 11/1997 |
| EP | 208975 | 1/1987 |
| EP | 1973588 | 11/2012 |
| FR | 2536285 | 5/1984 |
| GB | 805031 | 11/1958 |
| GB | 1360067 | 7/1974 |
| JP | 09512727 | 12/1997 |
| JP | 2001333980 | 12/2001 |
| KR | 1020160067391 | 6/2016 |
| WO | 9610430 | 4/1996 |
| WO | 2014061014 | 4/2014 |
| WO | 2015045180 | 4/2015 |

* cited by examiner

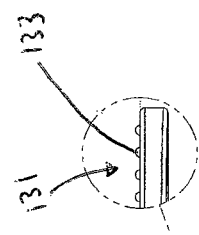
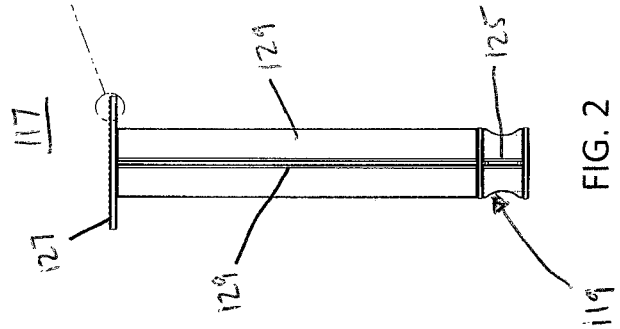
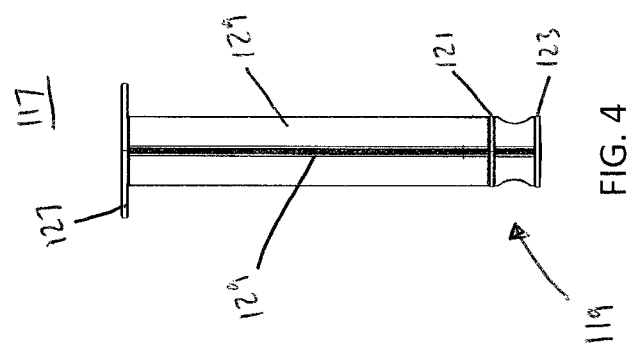
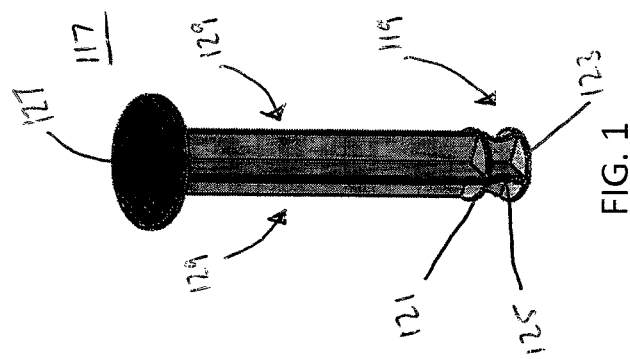

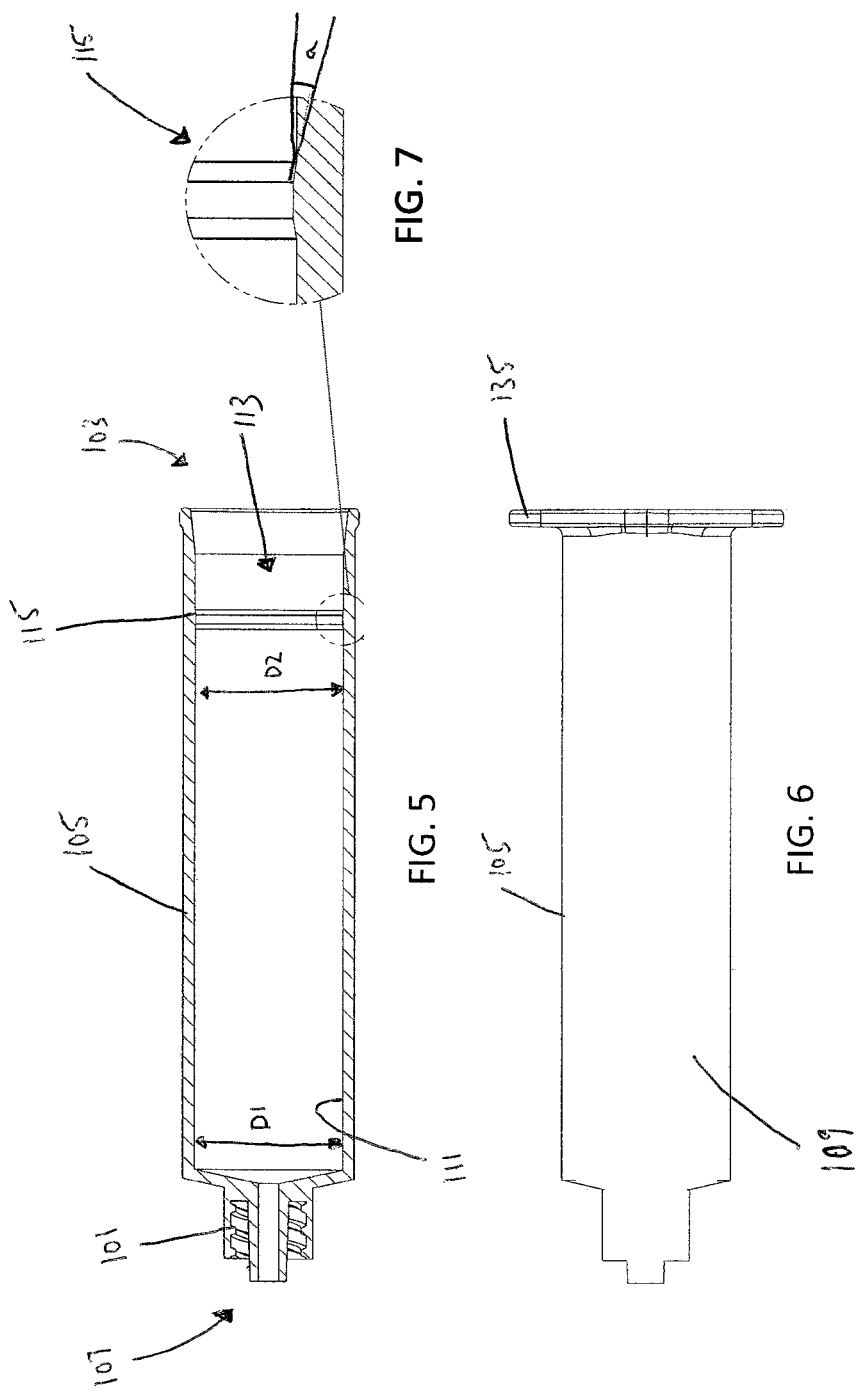

SYRINGE WITH POSITION LOCKING PLUNGER

CLAIM OF PRIORITY

This application claims priority to U.S. Application 62/396,876 filed on Sep. 20, 2016, the contents of which are herein fully incorporated by reference in its entirety.

FIELD OF THE EMBODIMENTS

The field of the embodiments of the present invention relate to syringes having locking mechanisms for maintaining a negative pressure (vacuum) therein. In particular, the embodiments are designed to enable a plunger to be locked in position, thereby freeing a user's hand from the plunger for other tasks.

BACKGROUND OF THE EMBODIMENTS

Syringes have a variety of medical and non-medical applications. In the medical field, syringes may be employed to withdraw bodily fluids, inject medications, and to aid in biopsy procedures. In the non-medical field, syringes may be utilized, for example, to withdraw samples of fluids or gases from reactors and to dispense adhesives or other fluid compositions.

A medical-based syringe generally includes a barrel and a plunger that is slidable within the barrel. The plunger may further have a piston that seals the barrel from within. The plunger commonly is provided with a finger grip at one end for pushing and pulling the plunger into and out of the barrel. The barrel often contains volume markings and typically the barrel is made of a translucent plastic material such that the position of the piston at the end of the plunger can be viewed through the barrel walls. The volumetric markings carried by the barrel are then aligned with the end of the piston to provide volumetric readings.

There are at least two major methods for syringe and needle procedures. One, where the operator controls the syringe and needle and an assistant controls a secondary medical device, or two, where the operator controls the syringe/needle and controls the secondary medical device. In many situations, an operator is not afforded the luxury of an assistant and thus it is advantageous to have a syringe that can be operated with one hand.

In order to achieve the single handed operation of the syringe, it is desirable to lock the plunger of a syringe at a given position within the barrel. For example, the piston may be retracted to a certain point within the barrel to provide a partial vacuum within the barrel, and the piston could then be positively prevented from returning toward its initial position. This enables the fluid or gas to be retained in the syringe until it can be discharged into an appropriate receptacle.

Review of Related Technology:

U.S. Pat. No. 5,685,864 pertains to an aspirator assembly enabled to remove fluids from a patient comprises an elongated hollow interior barrel, a plunger reciprocally movable within the barrel along the length thereof and extending outwardly from a rear end of the barrel. The plunger includes an elongated stem having a grip at an outer end thereof and a plunger head secured to an inner end of the stem. The plunger head is slidably engagable with an interior surface of the barrel. The improvement is found in a locking device which is selectively positionable into and out of a locked position. The locking device is formed in part on both the barrel and the stem and is adapted for removably locking the plunger head in a plurality of spaced apart locations within and along the length of the barrel. Additionally, the stem may be rotated so as to disengage the locking device and provide an aspirator with unobstructed reciprocation. Furthermore, a threaded stem connects the plunger head to the main plunger stem, so as to allow accurate adjustment of the aspirator volume by turning the handle. A flow control valve is provided at the second end of the barrel which allows selective closing of the end.

U.S. Pat. No. 5,215,536 pertains to a syringe for injecting medicinal fluids into a patient or aspirating fluids or tissue from a patient, wherein the syringe incorporates a self-locking mechanism on the plunger thus preventing the plunger from being withdrawn back into the barrel by the action of a vacuum in the syringe barrel. The self-locking mechanism is independent of the relative rotational relationship of the plunger with respect to the barrel. Unlocking may be effected by simply squeezing the self-locking mechanism on the plunger, no rotational force being necessary.

U.S. Pat. No. 4,711,637 pertains to a lock for a syringe which typically may be used with an aspirating biopsy needle. A malleable sheet defining a central, cutaway portion extending through the edge of the sheet and having foldable tabs positioned on the outer edge of the sheet is carried on a syringe barrel and may be used to lock the syringe plunger in a predetermined position. Thus a vacuum may be drawn in the syringe by the plunger with the plunger then being locked to provide suction to the aspirating biopsy needle.

U.S. Pat. No. 4,386,606 pertains to a syringe having a barrel and a plunger moveable axially in the barrel is provided with locking means for locking the plunger to the barrel. The locking means includes cam means carried between the barrel and the plunger, and means for moving the cam into a position forcing the plunger into binding contact with the barrel.

European Application 028975 pertains to a syringe for producing controlled vacuum suction for medical purpose, particularly for suctional puncture cytological studies, and optionally standard fluid injection functions like conventional syringes, of the general type comprising a cylinder finishing at the front end in a suction and/or injection tube designed for taking a corresponding needle, and inside the cylinder a plunger which, when it is displaced in the cylinder on the up stroke, produces a vacuum, wherein the cylinder and the plunger stem are provided with supplementary means for mutual locking designed for simple, swift anchoring of this stem in respect of the cylinder so as to maintain a desired vacuum by preventing the plunger to move back to the front end of the cylinder while carrying out vacuum suction, said locking being simply releasable, at the user's discretion; so that the plunger returns to its initial position and cancels the vacuum.

Various devices and methodologies are known in the art. However, their structure and means of operation are substantially different from the present disclosure. The present invention and its embodiments enables the syringe to have its plunger "locked" into position without the need for latches or switches or locks or slides or twisting, and the like. The design of the barrel and piston facilitate this "locking" interaction enabling one handed use of the syringe. At least one embodiment of this invention is presented in the drawings below and will be described in more detail herein.

SUMMARY OF THE EMBODIMENTS

Generally, the present invention and its embodiments provide for a syringe that enables one to "lock" or secure a position of a plunger, while the barrel is under a negative pressure, by simply removing the force applied to the plunger. In at least one embodiment, the syringe has at least a barrel, a tip, plunger, piston, coupling mechanism, and securement mechanism.

The syringe preferably has a coupling mechanism, such as a Luer lock, which may be coupled to hypodermic needles, catheters, intravenous ports/lines, and the like. Once appropriately coupled to a secondary device or inserted into the body, the plunger may be moved forward or retracted as needed. When the plunger is retracted, the plunger is configured to reside in place without engaging any additional moving mechanisms or rotating of the plunger, both of which can be cumbersome and could cause injury. Rather, the inner surface of the barrel is tapered allowing the piston to frictionably engage this tapered inner surface thereby preventing movement of the plunger when no pressure is being applied to the plunger. This holds true even if the plunger is holding a negative pressure within the barrel (below the piston).

Further, the barrel has a second feature, a positive stop or rise, which additionally prevents forward movement (towards the tip of the barrel) of the plunger. The positive stop is a rise in a section or sections of the inner surface of the barrel. This section rises about 10° about the plane of the barrel. The piston is shaped and configured to engage this positive stop. Thus, once the piston has been retracted beyond the positive stop, the shape of the bottom surface of the piston prevents movement of the piston over the positive stop. External pressure, such as by a user, must be applied to the plunger in order to overcome this plunger stopping feature.

In one embodiment of the present invention there is a syringe having a barrel body with a proximal end, a distal end, an outer surface, and an inner surface, the outer surface and inner surface defining a recess, wherein a coupling mechanism is located at the distal end of the barrel body, and wherein the inner surface is tapered from the distal end towards the proximal end of the barrel body; a securement mechanism disposed on the inner surface of the barrel body located proximate to the proximal end of the barrel body; and a plunger having a proximate and distal end, the plunger having a piston at the distal end, wherein the piston is configured to engage the securement mechanism disposed on the inner surface of the barrel body.

In another embodiment of the present invention there is a syringe having a barrel body with a proximal end, a distal end, an outer surface, and an inner surface, the outer surface and inner surface defining a recess, wherein a Luer lock mechanism is located at the distal end of the barrel body, and wherein the inner surface is tapered from the distal end towards the proximal end of the barrel body; a positive stop disposed on the inner surface of the barrel body located proximate to the proximal end of the barrel body, wherein the positive stop is a rise of about 10° configured to prevent movement of the piston once the piston has been retracted past the positive stop; a plunger having a proximate and distal end, the plunger having a piston at the distal end, wherein the piston is configured to engage the securement mechanism disposed on the inner surface of the barrel body.

In general, the present invention succeeds in conferring the following, and others not mentioned, benefits and objectives.

It is an object of the present invention to provide a syringe that can accommodate a variety of volumes of fluids and/or gases.

It is an object of the present invention to provide a syringe may be coupled to a number of secondary medical apparatuses.

It is an object of the present invention to provide a syringe that creates negative pressure by retracting the plunger.

It is an object of the present invention to provide a syringe that has a barrel taper configured to prevent forward movement of the plunger, unless force is applied to the plunger.

It is an object of the present invention to provide a syringe that contains a positive stop configured to prevent forward movement of the plunger once the plunger is retracted past the positive stop.

It is an object of the present invention to provide a syringe that is lightweight and durable.

It is an object of the present invention to provide a syringe that utilizes a Luer lock coupling mechanism.

It is an object of the present invention to provide a syringe that enables a user to operate the syringe, at times, with one hand.

It is an object of the present invention to provide a syringe that locks a position of the plunger without having to engage moving parts or twist the plunger.

BRIEF DESCRIPTION OF THE DRAWINGS

FIG. 1 is a perspective view of a plunger of an embodiment of the present invention.

FIG. 2 is a first side view of a plunger of an embodiment of the present invention.

FIG. 3 is a close up view of a top of a plunger of an embodiment of the present invention.

FIG. 4 is a second side view of an embodiment of the present invention.

FIG. 5 is a sectional side view of a syringe body of an embodiment of the present invention.

FIG. 6 is a side view of a syringe body of an embodiment of the present invention.

FIG. 7 is a close up view of a section of a syringe body having a positive stop.

DESCRIPTION OF THE PREFERRED EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Referring now to FIGS. 1-4, there are varying views of a plunger associated with an embodiment of the present invention. Generally, the present invention comprises a syringe capable of being coupled with a number of secondary devices such as catheters, intravenous ports/lines, and hypodermic and other types of needles.

As shown in the FIG. 1, the plunger 117 generally comprises at least a piston 119, flanges 129, retracting mechanism 127, upper surface of piston 121, and bottom surface of piston 123. As further shown in FIGS. 2 and 3, the plunger 117 may also have a retracting mechanism 127 with a plurality of ridges 133 disposed on a top surface 131 of the retracting mechanism 127.

The retracting mechanism 127 may be generally a flattened disk-like structure by which a user can retract or advance the plunger 117 and piston 119 through the barrel 105 (see FIGS. 5-6) thereby effectively up taking or expelling gases and/or fluids from the barrel 105. As noted above, in at least one embodiment, the retracting mechanism 127 has a plurality of ridges 133 upon a top surface 131 of the retracting mechanism 127. The ridges 133 (or other similar textured surface) allow for the user to adequately grip and manipulate the retracting mechanism 127 thereby operating the plunger 117.

The flanges 129 provide rigidity and support to the plunger 117 as a whole. The flanges 129 are coupled to an underside of the retracting mechanism 127 on one end, and coupled to the upper surface 121 of the piston 119 on the other end. The flanges 129 may be comprised of plastics, glasses, rubbers, metals, composites, and the like or some combination thereof. The flanges 129 may be formed from a continuous piece of material or may be separable from the retracting mechanism 127 and/or piston 119 or each other. In a preferred embodiment there are four flanges 129, however, the number of flanges 129 may vary from about one to about ten. It is preferable that the plunger 117, as a whole, is latex free.

The piston 119 comprises an upper surface 121 and a bottom surface 123. In between these two surfaces, there are any number of arced supports 125. The arced supports 125 provide rigidity to the piston 119 and further, in some embodiments, are shaped to engage structures of the barrel 105 such as the securement mechanism 115 (see FIG. 5). The piston 119 and its respective surfaces are configured to create a fluid (liquid and gas) tight seal between the walls of the barrel and the piston 119 itself. This is done without the use of an O-ring or other rubber or sealing member between the piston 119 and the inner surface of the barrel.

Referring now to FIGS. 5-7, there are varying views of a barrel 105 for which the plunger (described above) is intended to be inserted for use as a syringe. FIG. 5 provides a cutaway side view, whereas FIG. 6 provides a general outer view of the barrel 105.

As shown in FIGS. 5-6 there is generally at least a coupling mechanism 101, barrel 105, proximal end 103, distal end 107, inner surface 111, outer surface 109, recess 113, securement mechanism 115, and collar 135. The barrel 105 may be of varying sizes but is preferably a size that may accommodate up to about 10 cc (cubic centimeters) of fluid and/or gas. However, other sizes of barrels 105 are envisioned and contained within the purview of this invention. The barrel 105 may have lines or markings thereon to denote a particular volume.

The coupling mechanism 101 is preferably a Luer lock mechanism configured to couple to the requisite female Luer lock counterpart. This female counterpart may reside on a variety of objects including but not limited to catheters, intravenous ports/lines, and hypodermic needles.

The inner surface 111 of the barrel 105 is tapered in a way that enables the plunger, as shown in FIGS. 1-4, to frictionably engage the inner surface 111 without the need for an O-ring or rubber stopper covering the piston. For example, in FIG. 5 there are two different internal diameters D1 and D2 shown at corresponding locations within the barrel 105. In one embodiment, D1 may be about 0.628 inches and D2 may be about 0.620 inches. Thus, the inner surface 111 of the barrel 105 is tapered from the distal end 107 toward the proximal end 103. This taper can then interact with the piston 119 of the plunger 117 as shown in FIG. 4 as it travels along the length of the barrel.

Referring to FIG. 4, the piston 119 has an upper surface 121 and a bottom surface 123. In continuing the example above with D1 and D2, the upper surface 121 may be about 0.626 inches whereas the bottom surface 123 may be about 0.630 inches. This relationship, between the tapered inner surface and the piston 119, is thus readily apparent. However, these exact measurements or ratios need not necessarily be used. The relationship does need to be one that ensures that the piston and inner surface form a fluid and/or gas tight seal.

As one pulls back on the retracting mechanism 127 (when the plunger 117 is fully or partially inserted into the barrel), negative pressure is created within the barrel. The negative pressure can then be maintained, if pressure on the plunger 117 is not maintained, due to the interaction or relationship between the piston 119 and the inner surface 111 of the barrel 105 (see FIG. 5). Once the negative pressure has been achieved, the position of the piston and consequently the plunger can be maintained or is "locked" and the user is free to use the hand that would normally be required to reside on the retracting mechanism 127 for other tasks.

Further, referring now to FIGS. 5 and 7, there is a securement mechanism 115 in the form of a positive stop. The securement mechanism 115 is a ridge or rise in the inner surface 111 of the barrel 105. The securement mechanism 115 is located at a strategic point along the length of the barrel 105. As shown in FIG. 7, the angle $\alpha$ is formed between the securement mechanism 115 and the inner surface 111. Preferably this angle $\alpha$ is about 10°.

The securement mechanism 115 fully encircles the inner surface 111 of the barrel 105. There may be one or more ridges or rings encircling this inner surface 111. Once the piston has been retracted beyond the securement mechanism 115, the position of the plunger is secured. The piston is shaped such that the angle $\alpha$ formed by the securement mechanism 115 prevents forward movement of the plunger under the negative pressure.

Preferably the barrel and plunger are comprised only of plastics. Plastics used in construction of the syringe may include polyethylene terephthalate (PET), polyethylene (PE), high-density polyethylene, polyvinyl chloride (PVC), polyvinylidene chloride (PVDC), low-density polyethylene (LDPE), polypropylene (PP), polystyrene (PS), high impact polystyrene (HIPS) and polycarbonate (PC), or any combination thereof. Other materials may also be used while maintaining the spirit of the present invention and its embodiments.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A syringe comprising:
    a barrel body having a proximal end, a distal end, an outer surface, and an inner surface, the outer surface and inner surface defining an interior,
        wherein a coupling mechanism is located at the distal end of the barrel body, and
        wherein the inner surface is tapered from the distal end towards the proximal end of the barrel body;
    a securement mechanism disposed on the inner surface of the barrel body located proximate to the proximal end of the barrel body; and
    a plunger having a proximal and distal end, the plunger having a piston at the distal end of the plunger, wherein the piston is configured to engage the securement mechanism disposed on the inner surface of the barrel body, and wherein the securement mechanism is configured to prevent movement of the piston once the piston has been retracted past the securement mechanism towards the proximal end of the barrel body.

2. The syringe of claim 1 wherein the coupling mechanism is a Luer lock.

3. The syringe of claim 1 wherein the piston further comprises:

an upper surface;

a bottom surface; and a plurality of arced supports disposed therebetween.

4. The syringe of claim 3 wherein the upper surface has a diameter less than that of the bottom surface.

5. The syringe of claim 4 wherein the bottom surface has a diameter sized to engage the securement mechanism.

6. The syringe of claim 1 wherein the coupling mechanism of the barrel body is coupled to a hypodermic needle.

7. The syringe of claim 1 wherein the securement mechanism rises at about 10° from the inner surface of the barrel body.

8. The syringe of claim 1 wherein the piston is configured to create a fluid tight seal between the piston and the inner surface of the barrel body.

9. The syringe of claim 1 wherein the barrel body is configured to accommodate up to 10 cc of gas or fluid.

10. The syringe of claim 1 wherein the coupling mechanism is coupled to a catheter.

11. A syringe comprising:

a barrel body having a proximal end, a distal end, an outer surface, and an inner surface, the outer surface and inner surface defining an interior, wherein a Luer lock mechanism is located at the distal end of the barrel body, and wherein the inner surface is tapered from the distal end towards the proximal end of the barrel body;

a plunger having a proximal and distal end, the plunger having a piston at the distal end of the plunger, wherein the piston is configured to engage a securement mechanism disposed on the inner surface of the barrel body; and a positive stop disposed on the inner surface of the barrel body located proximate to the proximal end of the barrel body, wherein the positive stop is a rise of about 10° configured to prevent movement of the piston once an upper surface of the piston has been retracted past the positive stop towards the proximal end of the barrel body.

12. The syringe of claim 11 further comprising volumetric markings disposed on the barrel body.

13. The syringe of claim 11 further comprising a retracting mechanism disposed on the proximal end of the plunger.

14. The syringe of claim 13 wherein a top surface of the retracting mechanism has a plurality of ridges disposed thereon.

15. The syringe of claim 11 further comprising four flanges disposed along a vertical length of the plunger.

16. The syringe of claim 11 wherein retracting of the plunger causes the piston to engage the positive stop thereby preventing forward movement of the plunger once retraction of the plunger has ceased.

17. A syringe comprising:

a barrel body having a proximal end, a distal end, an outer surface, and an inner surface, the outer surface and inner surface defining an interior, wherein a Luer lock mechanism is located at the distal end of the barrel body, and wherein the inner surface is tapered from the distal end towards the proximal end of the barrel body;

a plunger having a proximal and distal end, the plunger having a piston at the distal end of the plunger, wherein the piston comprises an upper surface, a bottom surface, and at least one support disposed therebetween; and a positive stop disposed on the inner surface of the barrel body located proximate to the proximal end of the barrel body, wherein the bottom surface of the piston has a diameter sized to engage the positive stop, and wherein the positive stop is configured to prevent movement of the piston once the upper surface of the piston has been retracted past the positive stop towards the proximal end of the barrel body.

* * * * *